(12) United States Patent
Nakada et al.

(10) Patent No.: US 7,560,421 B2
(45) Date of Patent: Jul. 14, 2009

(54) METHOD OF DISINFECTING CONTACT LENS AND DISINFECTING LIQUID FOR THE METHOD

(75) Inventors: Kazuhiko Nakada, Nisshin (JP); Kotaro Sakanishi, Komaki (JP)

(73) Assignee: Menicon Co., Ltd., Nagoya-Shi (JP)

( * ) Notice: Subject to any disclaimer, the term of this patent is extended or adjusted under 35 U.S.C. 154(b) by 649 days.

(21) Appl. No.: 10/640,811

(22) Filed: Aug. 14, 2003

(65) Prior Publication Data

US 2004/0038956 A1 Feb. 26, 2004

(30) Foreign Application Priority Data

Aug. 20, 2002 (JP) .............................. 2002-238953
Aug. 5, 2003 (JP) .............................. 2003-286467

(51) Int. Cl.
*C11D 3/00* (2006.01)
*A01N 39/00* (2006.01)
*A61L 2/00* (2006.01)
*C09B 47/04* (2006.01)

(52) U.S. Cl. ...................... 510/112; 514/839; 514/840; 424/616; 422/28; 540/122; 540/131

(58) Field of Classification Search ................ 510/112, 510/113, 115; 514/185, 839, 840; 422/22, 422/24, 28; 424/616; 540/122, 131
See application file for complete search history.

(56) References Cited

U.S. PATENT DOCUMENTS

| 4,077,768 | A | * | 3/1978 | Johnston et al. ................ 8/107 |
| 4,318,883 | A | * | 3/1982 | Polony et al. ................ 422/22 |
| 4,394,125 | A | | 7/1983 | Hölzle et al. |
| 4,456,452 | A | | 6/1984 | Hölzle et al. |
| 4,568,517 | A | * | 2/1986 | Kaspar et al. ................ 422/30 |
| 4,634,555 | A | * | 1/1987 | Baxter et al. ................ 540/126 |
| 5,395,621 | A | | 3/1995 | Amtower |
| 5,910,473 | A | * | 6/1999 | Alfano et al. ................ 510/191 |
| 5,955,415 | A | * | 9/1999 | Gutierrez et al. ............ 510/312 |
| 6,004,510 | A | * | 12/1999 | Gilbert et al. ................ 422/29 |
| 6,149,842 | A | * | 11/2000 | Lally et al. ................ 264/1.36 |
| 6,165,954 | A | * | 12/2000 | Huth ................ 510/114 |
| 6,337,040 | B1 | | 1/2002 | Thakrar et al. |

FOREIGN PATENT DOCUMENTS

| DE | 0 984 041 | * | 8/2000 |
| EP | 1 095 664 A2 | | 5/2001 |
| JP | 52-109953 | | 9/1977 |
| JP | 62-153217 | | 7/1987 |
| JP | 63-59960 | | 3/1988 |
| JP | 63-264064 | | 10/1988 |
| JP | 02-139477 | | 5/1990 |
| JP | 06-073397 | | 3/1994 |
| JP | 06-321711 | | 11/1994 |
| JP | 2000-271194 | | 10/2000 |

OTHER PUBLICATIONS

Zumdahl, S., Chemistry, 2nd edition, 1989, D. C. Heath and Co.*

* cited by examiner

*Primary Examiner*—Michael G Hartley
*Assistant Examiner*—Leah Schlientz
(74) *Attorney, Agent, or Firm*—Burr & Brown

(57) ABSTRACT

A method of disinfecting a contact lens is provided, including the steps of preparing a disinfecting liquid which contains hydrogen peroxide and at least one metal phthalocyanine compound dispersed or dissolved in an aqueous medium, immersing the contact lens in the disinfecting liquid, and irradiating the disinfecting liquid in which the contact lens is immersed with a light.

13 Claims, No Drawings

METHOD OF DISINFECTING CONTACT LENS AND DISINFECTING LIQUID FOR THE METHOD

This application claims priority from Japanese Patent Application Nos. 2002-238953 filed on Aug. 20, 2002, and 2003-286467 filed on Aug. 5, 2003, respectively, the contents of which are incorporated herein by reference.

BACKGROUND OF THE INVENTION

1. Field of the Invention

The present invention relates in general to a method of disinfecting a contact lens and a disinfecting liquid used for the method, and more particularly to a technique for disinfecting the contact lens using a disinfecting liquid which is capable of exhibiting an excellent disinfecting effect.

2. Discussion of the Related Art

Conventionally, contact lenses are classified into non-water-contained or non-water-absorptive contact lenses and water-contained or water-absorptive contact lenses, or hard contact lenses and soft contact lenses. During a long period of use of the contact lenses, microorganisms such as bacteria and fungi tend to adhere to and proliferate on the surface of the contact lenses while the contact lenses are stored after they have been removed from the eyes. Such microorganisms may cause infectious diseases, giving adverse influences on the eyes of the lens user. In view of the above, the contact lenses need to be disinfected before they are worn on the eyes. In particular, it is indispensable to disinfect the soft contact lenses since the microorganisms are likely to proliferate on the surfaces of the soft contact lenses more often than on the hard contact lenses, increasing a risk of causing the infectious diseases.

A thermal disinfecting method using a suitable boiling and disinfecting device, and a chemical disinfecting method using a suitable chemical agent such as a disinfectant or a preservative have been used to disinfect contact lenses. The thermal disinfecting method inevitably requires a time-consuming boiling operation to disinfect the contact lenses. Accordingly, in recent years, the chemical disinfecting method has been widely employed to disinfect the contact lenses.

In the chemical disinfecting method, a liquid agent for contact lenses which contains a suitable disinfectant/preservative is used. The contact lenses are immersed in the liquid agent, so that the intended disinfecting treatment is conducted on the contact lenses. As the disinfectant/preservative contained in the contact lens liquid agent, JP-A-52-109953, JP-A-62-153217 and JP-A-63-59960 disclose chlorohexidine, benzalconium chloride and thimerosal, for instance.

When the contact lens is disinfected by the chemical disinfecting method, the disinfectant/preservative, such as chlorohexidine described above is generally contained in a relatively high concentration in the contact lens liquid agent, for the purpose of obtaining a sufficiently high degree of disinfecting effect. In this case, the disinfectant/preservative such as chlorohexidine is likely to be adsorbed on the contact lenses on a molecular level, deteriorating the wettability on the surface of the contact lenses and causing a change in the physical properties and configuration of the contact lenses. In some cases, the adsorption of the disinfectant/preservative on the contact lenses may cause various troubles with the eyes when the contact lenses are worn on the eyes. To keep the physical properties and configuration of the contact lenses from changing and to assure a high degree of safety to the eyes of the lens user, the contact lenses may be disinfected by using a liquid agent in which the disinfectant/preservative is contained in a relatively low concentration. In this case, however, the disinfecting effect to be exhibited by the liquid agent is inevitably lowered, causing contamination of the contact lenses by the microorganisms such as bacteria and fungi. Accordingly, when the contact lenses are disinfected by using such a conventional liquid agent, it is necessary to exercise an utmost care in adjusting the concentration of the disinfectant/preservative included in the liquid agent, making the disinfecting treatment of the contact lenses cumbersome.

As the disinfectant/preservative used in the chemical disinfecting method, hydrogen peroxide is also well known. When the hydrogen peroxide is used as the disinfectant/preservative, however, the concentration of the hydrogen peroxide needs to be generally as high as 3% (30000 ppm) to obtain an intended disinfecting effect.

The disinfectant/preservative contained in the contact lens liquid agent which is used in the chemical disinfecting method acts directly on the microorganisms such as bacteria and fungi, thereby exhibiting its disinfecting effect. Accordingly, the disinfectant/preservative is gradually decomposed and dissipated during use of the liquid agent, so that the liquid agent does not exhibit its disinfecting effect to a satisfactory extent. Thus, it is inevitably impossible to repeatedly use such a contact lens liquid agent, which may increase an economical burden on the lens user.

Metal phthalocyanine compounds are conventionally known as a catalyst having an oxidation-reduction function or ability. It is also known that a metal phthalocyanine compound exhibits a disinfecting effect with respect to harmful, pathogenic microorganisms based on its oxidation power, as disclosed in JP-A-6-321711, JP-A-63-264064, JP-A-2-139477, and JP-A-6-73397. However, it has never been known heretofore to use a metal phthalocyanine compound having a disinfecting effect for disinfecting contact lenses. Up to now, no techniques or methods have been known to effectively and safely disinfect contact lenses using a metal phthalocyanine compound.

SUMMARY OF THE INVENTION

The present invention was developed in the light of the background art situations described above. It is a first object of the present invention to provide a novel method of disinfecting a contact lens using a disinfecting liquid which exhibits an excellent disinfecting effect.

It is a second object of the invention to provide a contact lens disinfecting liquid which is advantageously used to practice such a disinfecting method.

An extensive study made by the inventors of the present invention under these situations has revealed that a contact lens can be effectively disinfected by immersing the contact lens in a disinfecting liquid which is obtained by dispersing or dissolving a metal phthalocyanine compound in an aqueous medium, and irradiating, with a light, the disinfecting liquid in which the contact lens is immersed. A further study by the inventors has revealed that the disinfecting liquid containing the metal phthalocyanine compound exhibits a significantly higher degree of disinfecting effect if the disinfecting liquid further contains a low concentration of hydrogen peroxide and if the disinfecting liquid containing the metal phthalocyanine and the hydrogen peroxide is irradiated with a light, than any disinfecting liquid which employs only one metal phthalocyanine compound and the hydrogen peroxide.

The above-indicated first object of the present invention may be attained according to a first aspect of the present invention, which provides a method of disinfecting a contact lens comprising the steps of (A) preparing a disinfecting liquid which contains at least one metal phthalocyanine compound represented by the following formula (I) and hydrogen peroxide, the at least one metal phthalocyanine compound being dispersed or dissolved in an aqueous medium;

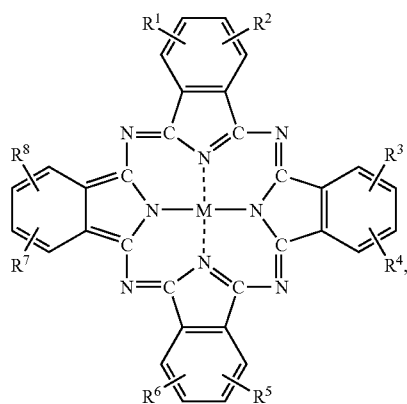

wherein M is zinc, aluminum, copper, iron, nickel, cobalt, gallium, aluminum chloride or gallium chloride, and each of $R^1$-$R^8$ is independently selected from a group consisting of a hydrogen atom, a halogen atom, a carboxyl group or an alkali metal or ammonium salt thereof, a sulfone group or an alkali metal or ammonium salt thereof, a quaternary ammonium group represented by the following formula (II), and an amine group represented by the following formula (III);

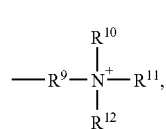

wherein $R^9$ is an alkylene group having 2-6 carbon atoms or an oxyalkylene group having 2-6 carbon atoms, and each of $R^{10}$-$R^{12}$ is independently selected from alkyl groups having 1-6 carbon atom(s),

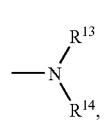

wherein each of $R^{13}$ and $R^{14}$ is independently selected from the group consisting of a hydrogen atom and —CO—A group in which A is an alkyl group having 7-17 carbon atoms, a vinyl group, 1-methylvinyl group, a methacryloyl group or an acryloyl group;

(B) immersing the contact lens in the disinfecting liquid; and (C) irradiating, with a light, the disinfecting liquid in which the contact lens is immersed.

The present method of disinfecting a contact lens described above employs the disinfecting liquid which contains, in an aqueous medium, at least one metal phthalocyanine compound represented by the above-indicated formula (I) and the hydrogen peroxide. While the contact lens to be disinfected is immersed in the disinfecting liquid, the disinfecting liquid is irradiated with a light for disinfecting the contact lens. The present method assures a synergistically enhanced disinfecting effect due to the disinfecting effect exhibited by the metal phthalocyanine compound together with the disinfecting effect exhibited by the hydrogen peroxide.

In the present method described above, the metal phthalocyanine compound contained in the disinfecting liquid is uniformly dispersed or dissolved in the disinfecting liquid in which the contact lens is immersed, without being aggregated or agglomerated around the contact lens. Accordingly, all of the molecules of the metal phthalocyanine compound are uniformly irradiated with a light, so that the disinfecting effect based on the oxidation power exhibited by the molecules of the metal phthalocyanine compound upon exposure to the light effectively works on the entire surface of the contact lens, whereby the contact lens can be sufficiently disinfected. Further, the disinfecting effect of the disinfecting liquid with respect to the contact lens is improved due to the hydrogen peroxide included in the disinfecting liquid. In the present method, the contact lens immersed in the disinfecting liquid can be easily and effectively disinfected simply by irradiating, with a light, the disinfecting liquid which includes the metal phthalocyanine compound and the hydrogen peroxide.

According to one preferred form of the above-described first aspect of the present invention, the at least one metal phthalocyanine compound is contained in the disinfecting liquid in a concentration in a range of 5-2000 ppm. This concentration permits the disinfecting liquid to have a sufficiently high degree of transparency, so that the irradiation of the light on the metal phthalocyanine compound is effectively improved, whereby the disinfecting effect of the metal phthalocyanine compound with respect to the contact lens can be significantly enhanced.

In another preferred form of the above-described first aspect of the present invention, the hydrogen peroxide is contained in the disinfecting liquid in a concentration in a range of 1-300 ppm. The disinfecting liquid used in the present method advantageously exhibits an excellent disinfecting effect even if the concentration of the hydrogen peroxide is relative low. The use of the hydrogen peroxide in such a low concentration is effective to considerably reduce adverse influences on the eye of the lens user, to thereby assure the lens user of a high degree of safety.

In still another preferred form of the above-described first aspect of the present invention, the light with which the disinfecting liquid is irradiated has a wavelength in a range of 550-750 nm. The photocatalytic action of the metal phthalocyanine compound contained in the disinfecting liquid is advantageously promoted by irradiation with the light whose wavelength is held in the range described above, so that the disinfecting liquid exhibits an excellent disinfecting effect.

In still another preferred form of the above-described first aspect of the present invention, the disinfecting liquid further contains at least one of a chelating agent, an isotonic agent, a buffer, a surfactant, a thickener, and a preservative. According to this arrangement, the disinfecting liquid has an intended property given by the at least one component to be added.

The contact lens to be disinfected according to the present method includes various known contact lenses such as an oxygen-permeable lens, a non-water-absorptive contact lens, a water-absorptive contact lens, etc. When a water-absorptive contact lens is disinfected according to the present method, the disinfecting liquid is preferably a dispersion liquid in which the at least one metal phthalocyanine compound is dispersed, for preventing the water-absorptive contact lens from being colored by the metal phthalocyanine compound.

According to a second aspect of the present invention, a contact lens disinfecting liquid is provided which exhibits a disinfecting effect with respect to a contact lens by being irradiated with a light, the contact lens disinfecting liquid containing, in an aqueous medium, at least one metal phthalocyanine compound represented by the above-indicated formula (I) and hydrogen peroxide.

The present disinfecting liquid described above contains, in an aqueous medium, at least one metal phthalocyanine compound represented by the above-indicated formula (I) and hydrogen peroxide, the at least one metal phthalocyanine compound being dispersed or dissolved in the aqueous medium. With the contact lens to be disinfected being immersed in the disinfecting liquid, the disinfecting liquid is irradiated with a light, so that the disinfecting liquid advantageously exhibits a disinfecting effect with respect to the contact lens, based on the photocatalytic action of the metal phthalocyanine compound. The present disinfecting liquid assures a synergistically enhanced disinfecting effect due to the disinfecting effect exhibited by the metal phthalocyanine compound together with the disinfecting effect exhibited by the hydrogen peroxide. Since the metal phthalocyanine compound included in the disinfecting liquid functions as a catalyst, the disinfecting efficacy of the metal phthalocyanine compound lasts for a long period of time.

DETAILED DESCRIPTION OF THE INVENTION

The present method of disinfecting a contact lens is characterized by preparing a disinfecting liquid which contains, in an aqueous medium, at least one suitable metal phthalocyanine compound having photoactivity and hydrogen peroxide, immersing a contact lens to be disinfected in the disinfecting liquid, and irradiating the disinfecting liquid in which the contact lens is immersed with a light, so that the contact lens is disinfected.

The metal phthalocyanine compound used in the contact lens disinfecting liquid according to the present invention is a catalyst having oxidation-reduction function or ability. The metal phthalocyanine compound is uniformly dispersed or dissolved in the aqueous medium. The metal phthalocyanine compound exhibits a high degree of oxidation power upon exposure to a light, so that the contact lens can be disinfected due to an effective disinfecting effect based on the oxidation power exhibited by the metal phthalocyanine compound upon exposure to the light.

In the present invention, the metal phthalocyanine compound represented by the above-indicated formula (I) is suitably used.

In the formula (I), "M" is zinc, aluminum, copper, iron, nickel, cobalt, gallium, aluminum chloride (AlCl) or gallium chloride (GaCl). For assuring high degrees of disinfecting effect and safety, copper, iron or zinc is preferable.

In formula (I), each of "$R^1$-$R^8$" is independently selected from the group consisting of a hydrogen atom, a halogen atom, a carboxyl group (—COOH) or its alkali metal or its ammonium salt (e.g., —COONa, —COONH$_4$), a sulfone group (—SO$_3$H) or its alkali metal or its ammonium salt (e.g., —SO$_3$Na, —SO$_3$NH$_4$), a quaternary ammonium group represented by the above-indicated formula (II), and an amine group represented by the above-indicated formula (III). For imparting excellent water solubility to the metal phthalocyanine compound, a carboxyl group, its alkali metal or its ammonium salt, or a sulfone group, its alkali metal or its ammonium salt are preferable.

In the above-indicated formula (II), "$R^9$" is an alkylene group having 2-6 carbon atoms or an oxyalkylene group having 2-6 carbon atoms. Examples of the alkylene group having 2-6 carbon atoms include: a linear alkylene group such as an ethylene group or a trimethylene group; and a branched alkylene group such as a propylene group or a β-butylene group. Examples of the oxyalkylene group having 2-6 carbon atoms include an oxyethylene group and an oxypropylene group. Each of "$R^{10}$-$R^{12}$" in the above-indicated formula (II) is independently selected from alkyl groups having 1-6 carbon atom(s). Examples of the alkyl groups having 1-6 carbon atom(s) include a methyl group, an ethyl group, a propyl group, and a butyl group.

In the above-indicated formula (III), "$R^{13}$" and "$R^{14}$" are each independently selected from the group consisting of a hydrogen atom and —CO—A group in which "A" is an alkyl group having 7-17 carbon atoms, a vinyl group, 1-methylvinyl group, a methacryloyl group or an acryloyl group. Examples of the alkyl group having 7-17 carbon atoms include a heptyl group and an octyl group.

At least one kind of metal phthalocyanine compound represented by the above-indicated formula (I) is suitably selected and contained in the aqueous medium. The metal phthalocyanine compound used in the present invention may be highly soluble or not highly soluble to water, or insoluble to water, depending upon which kind of "$R^1$-$R^8$" is used as a substituent in the formula (I). A water-soluble metal phthalocyanine compound is uniformly dissolved in the aqueous medium, so that a water-soluble metal phthalocyanine compound is uniformly contained in the aqueous medium. Where the disinfecting liquid includes a metal phthalocyanine compound which is not highly soluble to water or insoluble to water, such a metal phthalocyanine compound needs to be uniformly or homogeneously dispersed in the aqueous medium without being aggregated or precipitated at least when the light is incident on the disinfecting liquid, to permit the metal phthalocyanine compound to exhibit its disinfecting effect. According to this arrangement, the uniformly dispersed metal phthalocyanine compound is sufficiently and evenly irradiated with the light, to thereby exhibit an intended high degree of disinfecting effect. The contact lens disinfecting liquid according to the present invention may be a dissolution-type liquid agent wherein the metal phthalocyanine compound is dissolved in the aqueous medium, or a dispersion-type liquid agent wherein the metal phthalocyanine compound is dispersed in the aqueous medium. For obtaining a higher degree of disinfecting effect, the disinfecting liquid is preferably the dissolution-type liquid agent.

The disinfecting effect exhibited by the metal phthalocyanine compound is due to its catalytic action. In this respect, unlike the disinfectant/preservative such as the chlorohexidine used in the conventional chemical disinfecting method, the metal phthalocyanine compound is not decomposed or dissipated during use of the disinfecting liquid, so that the disinfecting liquid exhibits a long-term or lasting disinfecting effect. Therefore, the disinfecting liquid can be repeatedly used while permitting the metal phthalocyanine compound to exhibit the disinfecting effect.

The metal phthalocyanine compound used as the disinfecting component in the present contact lens disinfecting liquid is also used to color the contact lens, such that the metal phthalocyanine compound is bonded to, or contained in the material of the contact lens. When the contact lens is disinfected by using the disinfecting liquid which contains such a metal phthalocyanine, the contact lens does not suffer from a change in its physical properties and configuration even if a small amount of the metal phthalocyanine compound is adsorbed on the surface of the contact lens or introduced into the contact lens.

Since the oxidation power of the metal phthalocyanine compound is effectively increased by being irradiated with the light, it is possible to attain a good disinfecting effect even if the amount of the metal phthalocyanine compound included in the disinfecting liquid is significantly small. While the concentration of the metal phthalocyanine compound in the disinfecting liquid varies depending upon the kind of the metal phthalocyanine compound to be used, it is held generally in a range of 5-2000 ppm, preferably in a range of 20-1500 ppm, more preferably in a range of 50-1200 ppm. The concentration of the metal phthalocyanine compound held in the range described above is effective to provide a significantly high degree of disinfecting effect. If the concentration of the metal phthalocyanine compound is excessively low, the disinfecting effect exhibited by the metal phthalocyanine is insufficient. If the concentration of the metal phthalocyanine compound is excessively high, on the other hand, the transparency of the disinfecting liquid is lowered. In this case, the entirety of the disinfecting liquid is not effectively irradiated with the incident light, deteriorating the disinfecting effect or making it difficult to visually confirm or observe the presence of the contact lens immersed in the disinfecting liquid. If the metal phthalocyanine compound is used in a concentration exceeding the upper limit of 2000 ppm, the contact lens may be undesirably colored by the metal phthalocyanine compound which also functions as a coloring agent or dye, depending upon the kind of the metal phthalocyanine compound to be used.

The hydrogen peroxide used in combination with the above-described metal phthalocyanine compound in the present contact lens disinfecting liquid exhibits a disinfecting effect, owing to a strong oxidative action or power of hydroxyradical formed upon decomposition of the hydrogen oxide even where the hydrogen peroxide is used alone. In the present disinfecting liquid, the hydrogen peroxide is also effective to promote the disinfecting effect exhibited by the metal phthalocyanine compound.

Due to the combined use of the metal phthalocyanine compound represented by the above-indicated formula (I) and the hydrogen peroxide, the catalytic action of the metal phthalocyanine compound is promoted, and the disinfecting liquid exhibits a synergistically enhanced disinfecting effect due to the disinfecting effect exhibited by the metal phthalocyanine compound together with the disinfecting effect exhibited by the hydrogen peroxide, as compared in a case wherein only one of the metal phthalocyanine compound and the hydrogen peroxide is used.

Since the combined use of the hydrogen peroxide and the metal phthalocyanine compound assures a significantly high degree of disinfecting effect, the concentration of the hydrogen peroxide can be reduced to $1/100$ or lower of the concentration (generally 3%=30000 ppm) required in a case wherein only the hydrogen peroxide is used as the disinfecting component. Accordingly, the concentration of the hydrogen peroxide in the present disinfecting liquid is preferably held in a range of 1-300 ppm. Since the hydrogen peroxide is contained in the disinfecting liquid in a considerably low concentration as described above, it is not necessary to carry out a neutralization treatment for neutralizing the hydrogen peroxide generally conducted in a conventional disinfecting liquid containing the hydrogen peroxide, in other words, it is not necessary to carry out a treatment to decompose and thereby detoxify the hydrogen peroxide. Accordingly, the present disinfecting method enjoys high economy and a high degree of disinfecting efficiency. Since the concentration of the hydrogen peroxide is sufficiently low as described above, the eye of the lens user is less likely to be adversely influenced by the hydrogen peroxide even if the contact lens which has been disinfected with the present contact lens disinfecting liquid is worn on the eye with the disinfecting liquid remaining on the surface or in the inside of the contact lens without being decomposed.

When the concentration of the hydrogen peroxide is less than 1 ppm, the effect to be favorably exhibited by the hydrogen peroxide is not sufficiently obtained. When the concentration of the hydrogen peroxide exceeds 300 ppm, on the other hand, the hydrogen peroxide tends to remain on the surface or in the inside of the contact lens though the disinfecting effect to be obtained is high. In this case, the eye of the lens user may suffer from advance influences or serious troubles, so that the neutralization treatment needs to be conducted in some cases, undesirably making the disinfecting treatment of the contact lens cumbersome.

The contact lens disinfecting liquid containing hydrogen peroxide may further include, as needed, a substance such as Fe ion(s) that causes a Fenton reaction, for increasing the activity of the hydrogen peroxide to thereby effectively form the hydroxyradical. The addition of such a substance is effective to further increase the disinfecting effect exhibited by the disinfecting liquid.

The contact lens disinfecting liquid according to the present invention may further contain, as needed, various known additives as used in the conventional contact lens liquid agent, in addition to the above-described substance that causes the Fenton reaction. For instance, the present disinfecting liquid may further contain at least one of a chelating agent, an isotonic agent, a buffer, a surfactant, a thickener, and a preservative. The additives to be contained in the disinfecting liquid should be safe to the living body and ophthalmically physiologically acceptable, and should not give adverse influences on the effects provided by the metal phthalocyanine compound and the hydrogen peroxide. The additives are contained in the disinfecting liquid in amounts that do not inhibit the effects provided by the metal phthalocyanine compound and the hydrogen peroxide.

The chelating agent to be added, as needed, as one of the additives to the present contact lens disinfecting liquid is effective to prevent metal ions, such as calcium included in the disinfecting liquid or the tear fluid adhering to the contact lens, from being deposited on the contact lens. Examples of the chelating agent include ethylenediaminetetraacetic acid or a sodium salt or iron complex thereof, phytic acid, citric acid, etc. The chelating agent is not limited to those described above. The chelating agent is contained in the disinfecting liquid generally in a concentration of 0.001-0.1 mol/L, preferably 0.0015-0.05 mol/L, for obtaining a sufficiently high degree of the effect of preventing the deposition of the calcium etc., on the contact lens. If the concentration of the chelating agent is less than 0.001 mol/L, the deposition of the calcium etc. on the contact lens is not effectively prevented. The concentration of the chelating agent exceeding 0.1 mol/L does not significantly enhance the effect of preventing the deposition of the calcium etc., resulting in poor economy.

The isotonic agent is a component that adjusts the osmotic pressure of the contact lens disinfecting liquid to be substantially equal to that of the tear fluid, i.e., 280-300 mOsm/kg, and permits the contact lens to maintain its shape with high stability while the contact lens is stored and immersed in the disinfecting liquid. Any known isotonic agents may be used, as long as they are ophthalmically physiologically acceptable. Examples of the isotonic agent include inorganic salts such as sodium chloride, potassium chloride, and calcium chloride, and buffers described later.

For permitting the disinfecting liquid to have the desired osmotic pressure, the amount of the isotonic agent included in the contact lens disinfecting liquid is generally not smaller than 0.01 mol/L, preferably not smaller than 0.05 mol/L. When the amount of the isotonic agent is excessively large, the osmotic pressure of the disinfecting liquid becomes excessively high, giving adverse influences on the shape of the contact lens. In view of this, the isotonic agent is included in the disinfecting liquid in an amount of not greater than 0.5 mol/L, preferably not greater than 0.15 mol/L. According to this arrangement, the osmotic pressure of the disinfecting liquid is made substantially equal to that of the tear fluid, so that the lens user does not suffer from eye irritation even if the disinfecting liquid remaining on and adhering to the surface of the contact lens gets into the eye when the disinfected contact lens is worn on the eye.

The buffer is a component to maintain the pH of the disinfecting liquid at a constant level which is close to the pH of the tear fluid, i.e., in a range of about 5-9, to prevent a change of the pH of the disinfecting liquid due to external factors, and to protect the configuration and the physical properties such as the optical characteristics of the contact lens during its storage in the disinfecting liquid. Any known buffers may be used, as long as they are ophthalmically physiologically acceptable. Typical examples of the buffer include boric acid and its sodium salt, phosphoric acid and its sodium salt, citric acid and its sodium salt, lactic acid and its sodium salt, amino acid such as glycine or glutamic acid and a sodium salt of the amino acid, and malic acid and its sodium salt.

The surfactant to be added, as needed, to the present contact lens disinfecting liquid is a component to give the disinfecting liquid an activity for cleaning the contact lens, in addition to the disinfecting effect. At least one of an anionic surfactant and a nonionic surfactant which are generally used in the conventional contact lens liquid agent is advantageously employed, so that the disinfecting liquid exhibits a cleaning effect for removal of the lipid, etc., from the contact lens.

Typical examples of the anionic surfactant include sodium alkylsulfate, sodium alkylbenzene sulfonate, sodium alkyloylmethyl taurine, sodium alkyloylsarcosine, sodium α-olefinsulfonate, sodium polyoxyethylenealkyl ether phosphate, sodium polyoxyethylenealkyl ether sulfate, sodium polyoxyethylenealkylphenyl ether sulfate, sodium di(polyoxyethylenealkyl ether) phosphate, etc. Among those anionic surfactants, the sodium alkylsulfate, sodium alkylbenzene sulfonate, sodium α-olefinsulfonate, sodium polyoxyethylenealkyl ether sulfate, and sodium polyoxyethylenealkylphenyl ether sulfate exhibit an excellent cleaning effect, and an especially high cleaning effect when used in combination with the nonionic surfactant even if the period of time during which the contact lens is immersed for storage in the disinfecting liquid is relatively short.

In order to provide a sufficiently high degree of a cleaning effect to the contact lens disinfecting liquid, the amount of the anionic surfactant to be included in the disinfecting liquid is generally not smaller than 0.01 w/v %, preferably not smaller than 0.02 w/v %. The cleaning effect does not significantly increase even if the amount of the anionic surfactant is excessively large. The excessively large amount of the anionic surfactant may even cause undesirable troubles such as roughening of the hand skins. In view of this, the anionic surfactant is included in the disinfecting liquid in an amount of generally not greater than 10 w/v %, preferably not greater than 5 w/v %.

Typical examples of the nonionic surfactant include polyethylene glycol adduct of higher alkylamine, polyethylene glycol adduct of higher fatty acid amide, polyglycerin ester of higher fatty acid, polyethylene glycol ester of higher fatty acid, polyalkylene glycol ester of higher fatty acid, polyethylene glycol copolymer ester, polyhydric alcohol addition compound of polyethylene glycol ester of higher fatty acid, polyethylene glycol ether of higher alcohol, polyglycerin ether of higher alcohol, polyethylene glycol ether of alkylphenol, formaldehyde condensation product of polyethylene glycol ether of alkylenephenol, polypropylene glycol-polyethylene glycol copolymer, phosphate, castor oil, hardened castor oil, polyethylene glycol sorbitan alkylester, polyethylene glycol addition compound of sterol, polyoxyethylene polyoxypropylene glycol, etc. Among these nonionic surfactants, it is preferable to use the polyethylene glycol ether of higher alcohol, polyethylene glycol ester of higher fatty acid, polyglycerin ester of higher fatty acid, polyethylene glycol ether of alkylphenol, polyethylene glycol sorbitan alkylester, and polyoxyethylene polyoxypropylene glycol, for obtaining an excellent cleaning effect.

Like the anionic surfactant described above, the nonionic surfactant is included in the contact lens disinfecting liquid in an amount of generally not smaller than 0.01 w/v %, preferably not smaller than 0.02 w/v %, for permitting the disinfecting liquid to exhibit a sufficiently high degree of cleaning effect. The cleaning effect does not significantly increase even if the amount of the nonionic surfactant is excessively large. The excessively large amount of the nonionic surfactant may even cause undesirable troubles such as roughening of the hand skins. In view of this, the nonionic surfactant is included in the disinfecting liquid in an amount of generally not greater than 10 w/v %, preferably not greater than 5 w/v %.

When the anionic surfactant and the nonionic surfactant are used in combination, the amount of the anionic and nonionic surfactants to be included in the disinfecting liquid is preferably determined such that the amounts of the anionic and nonionic surfactants are held in the respective ranges described above, and such that the total amount of the anionic and nonionic surfactants are held generally in a range of 0.02-20 w/v %, preferably in a range of 0.04-10 w/v %.

The thickener is used to adjust the viscosity of the disinfecting liquid and to protect the contact lens from external physical forces while the contact lens is stored in the disinfecting liquid. Any known thickeners may be used, as long as they are ophthalmically physiologically acceptable. Examples of the thickener include polyvinyl alcohol, poly-N-vinyl pyrrolidone, polyacrylamide and its hydrolyzed product, polyacrylic acid, xanthan gum, hydroxyethyl cellulose, carboxymethyl cellulose, methylhydroxyethyl cellulose, methylhydroxypropyl cellulose, methyl cellulose, sodium alginate, polyethylene glycol, gelatin, sodium chondroitin sulfate, sodium hyaluronate, gum arabic, guar gum, etc.

For protecting the contact lens from external stresses or forces while the contact lens is stored in the disinfecting liquid, the lower limit of the amount of the thickener included in the disinfecting liquid is generally 0.01 w/v %, preferably 0.02 w/v %. The upper limit of the amount of the thickener is generally 10 w/v %, preferably 5 w/v % to prevent deterioration of the storage stability of the disinfecting liquid due to its gellation which would arise from the use of excessively large amount of the thickener.

Like the metal phthalocyanine compound and the hydrogen peroxide used in the present invention, the preservative is effective to prevent the disinfecting liquid from being contaminated by the microorganisms such as bacteria and fungi, and also to prevent the contact lens from being contaminated by various bacteria and fungi while the contact lens is stored in the disinfecting liquid. In the present invention, the preservative is used as an auxiliary component of the metal phthalocyanine compound and the hydrogen peroxide, so that the disinfecting liquid including the preservative exhibits a further enhanced disinfecting effect. Any known preservatives may be used, as long as they are ophthalmically physiologically acceptable. Typical examples of the preservative include: a mercury-based preservative such as phenyl mercury nitrate, phenyl mercury acetate, or thimerosal; a surfactant-based preservative such as benzalconium chloride or pyridinium bromide; an alcohol-based preservative such as chlorohexidine, polyhexamethylene biguanide, or chlorobutanol; methyl paraben; propyl paraben; dimethylol dimethylhydantoin; and imidazolium urea.

For permitting the disinfecting liquid to exhibit a higher disinfecting effect, the lower limit of the amount of the preservative included in the disinfecting liquid is generally 0.05 ppm, preferably 0.1 ppm. When the amount of the preservative included in the disinfecting liquid is excessively large, the preservative may get directly in the eye of the lens user to cause undesirable troubles with the eye and cause adverse influences on the specifications and physical properties of the contact lens, depending upon the kind of the preservative used. In view of this, it is preferable that the upper limit of the amount of the preservative is generally 50 ppm, preferably 30 ppm.

The present contact lens disinfecting liquid which contains the metal phthalocyanine compound, the hydrogen peroxide, and the other components as described above is easily prepared in the usual manner for preparing an aqueous solution, without requiring any special procedure. The present disinfecting liquid is prepared by dissolving or dispersing each component in the aqueous medium.

As the aqueous medium in which the various components are included, there may be employed a solution which is principally constituted by water such as a saline solution and a known contact lens storing or cleaning solution, in addition to water such as tap water, purified water, and distilled water.

In the present invention, the contact lens to be disinfected is immersed in the contact lens disinfecting liquid wherein the metal phthalocyanine compound, hydrogen peroxide, and various components described above are included. The disinfecting liquid in which the contact lens is immersed is irradiated with a light, so that the contact lens is disinfected.

In the disinfecting treatment using the disinfecting liquid descried above, the disinfecting liquid is accommodated in a suitable container at least a part of which permits a light to pass therethrough, and the contact lens to be disinfected is immersed in the disinfecting liquid accommodated in the container. Then, the container is irradiated with a suitable light so that the light is incident on the disinfecting liquid (the metal phthalocyanine and the hydrogen peroxide) in the container, whereby the contact lens is disinfected. In this disinfecting method, the container is preferably formed of a transparent material, and is irradiated with the light in a plurality of directions for increased irradiation efficiency.

When the metal phthalocyanine compound which is not highly soluble to water is used, it is preferable to apply ultrasonic waves to the disinfecting liquid or oscillate the disinfecting liquid, e.g., by oscillating the container in which the disinfecting liquid is accommodated, for instance, prior to or upon application of the light. According to this arrangement, the metal phthalocyanine compound in the disinfecting liquid can be uniformly dispersed, resulting in an enhanced disinfecting effect.

The light to be applied to the disinfecting liquid in which the contact lens is immersed preferably has a wavelength in a general range of 350-800 nm, for effectively promoting the photocatalytic reaction in the metal phthalocyanine compound. It is more preferable that the light to be applied to the disinfecting liquid has a wavelength in a range of 550-750 nm, since the absorption wavelength of the metal phthalocyanine compound represented by the above-indicated formula (I) exists in that wavelength range, so that the catalytic action of the metal phthalocyanine compound can be advantageously increased. The light source is not particularly limited, as long as the wavelength of the light is held in the range of 350-800 nm. For instance, the light may be a natural light such as sunlight. Alternatively, the light may be emitted from an artificial light source. Such a light source may be an LED (light-emitting diode), a laser source, an incandescent lamp, a super-high pressure mercury lamp, a fluorescent lamp or a xenon lamp. The intensity of the light is not particularly limited, but is suitably determined depending upon the light source to be used by considering that the excessively low light intensity is not sufficient to effectively increase the catalytic action of the metal phthalocyanine compound while the excessively high light intensity may cause deterioration of the contact lens immersed in the disinfecting liquid such as a change of its color to yellow.

The period of time during which the contact lens is disinfected by the disinfecting liquid while it is exposed to the light described above is suitably determined depending upon a desired degree of disinfection of the contact lens, and various factors such as the kind of the contact lens to be disinfected, and the wavelength and the intensity of the light to be applied to the disinfecting liquid. For obtaining a sufficiently high degree of disinfecting effect, the disinfecting liquid needs to be irradiated with the light for at least five minutes. For an efficient disinfecting treatment, the disinfecting liquid is irradiated with the light for a period of time up to about twelve hours, preferably up to six hours.

According to the present method, the contact lens can be sufficiently and easily disinfected without causing adverse influences on the contact lens (such as a change in its base curve) or making the handling of the disinfecting liquid difficult, simply by irradiating the disinfecting liquid that contains the metal phthalocyanine compound and the hydrogen peroxide with the light for a prescribed time period.

The contact lens which has been disinfected according to the present method is removed from the disinfecting liquid and worn on the eye of the lens user. When the disinfecting liquid includes the hydrogen peroxide in a concentration held in the above-described range (1-300 ppm), the amount of the hydrogen peroxide remaining in the disinfecting liquid is extremely small, i.e., almost zero, so that it is not necessary to conduct a neutralization treatment to neutralize the residual hydrogen peroxide. Accordingly, the contact lens taken out of the disinfecting liquid may be directly worn on the eye of the lens user. Alternatively, the disinfected contact lens may be rinsed with a saline, etc., prior to wearing on the eye.

The kind of the contact lenses to be disinfected according to the present disinfecting method is not particularly limited. For instance, the present disinfecting method can be applied to a water-absorptive contact lens, a non-water-absorptive contact lens, a hard contact lens, and a soft contact lens, irrespective of the materials of the contact lenses. Here, the water-absorptive contact lens is defined as a contact lens whose water content is not smaller than 10% while the non-water-absorptive contact lens is defined as a contact lens whose water content is less than 10%.

The water-absorptive contact lens tends to be colored by the metal phthalocyanine compound, which is blue or green, and which gets into the water-absorptive contact lens. In view of this, when a water-absorptive contact lens is disinfected according to the present method, it is preferable to use the dispersion-type disinfecting liquid, wherein the metal phthalocyanine compound is uniformly dispersed, rather than the dissolution-type disinfecting liquid, since the metal phthalocyanine compound dispersed in the disinfecting liquid is less likely to get into the contact lens than that dissolved in the disinfecting liquid.

While the contact lens disinfecting liquid according to the present invention is used to disinfect the contact lens, the disinfecting liquid which exhibits its disinfecting effect by exposure to the light can be used as a contact lens storing solution. For instance, during transportation of the contact lenses, the contact lenses are accommodated in a suitable transportation container, together with the disinfecting liquid according to the present invention, which container permits light transmission. In this case, the contact lenses in the container are stored in a disinfected state with the disinfecting liquid being irradiated with natural light during the transportation of the contact lenses.

EXAMPLES

To further clarify the concept of the present invention, some examples of the invention will be described. It is to be understood that the invention is not limited to the details of the illustrated examples and the foregoing description, but may be embodied with various changes, modifications and improvements, which may occur to those skilled in the art without departing from the scope of the invention defined in the attached claims.

Preparation of Disinfecting Liquid Specimens

Preparation of Solutions or Dispersion Liquids of the Metal Phthalocyanine Compounds There were prepared various kinds of solutions or dispersion liquids of the metal phthalocyanine compounds having a prescribed concentration, by dissolving or dispersing, in distilled water, various metal phthalocyanine compounds represented by the above-indicated formula (I) wherein "M" and "$R^1$-$R^8$" are those indicated in the following Table 1.

(2) Preparation of a Hydrogen Peroxide Solution

There was prepared a hydrogen peroxide solution having a prescribed concentration, by dissolving the hydrogen peroxide in distilled water.

(3) Preparation of an Aqueous Solution of $FeCl_3 \cdot 6H_2O$

There was prepared an aqueous solution of $FeCl_3$ having a prescribed concentration, by dissolving, in distilled water, iron chloride hexahydrate ($FeCl_3 \cdot 6H_2O$).

Various disinfecting liquid specimens Nos. 1-13 were prepared by suitably mixing the solutions or dispersion liquids of the metal phthalocyanine compounds prepared according to the above process (1), the hydrogen peroxide solution prepared according to the process (2), and the aqueous solution of $FeCl_3$ prepared according to the process (3), such that the concentrations of the metal phthalocyanine compound, hydrogen peroxide, and iron chloride are adjusted to respective values as indicated in the Table 1.

Test for Examining the Disinfecting Effect

Each of the thus prepared disinfecting liquid specimens Nos. 1-13 was examined to determine its disinfecting effect in the following manner. Initially, *Pseudomonas aeruginosa* IFO 13275 as the microbial challenge organism was inoculated into respective disinfecting liquid specimens Nos. 1-13, so that each disinfecting liquid specimen was adjusted to $10^6$ cfu/mL. 0.2 mL of each disinfecting liquid specimen into which the microbial challenge organism had been inoculated was accommodated into a sterile, transparent plate.

The plates in which the disinfecting liquid specimens Nos. 1-8 and 13 are accommodated, respectively, were irradiated with various lights as indicated in Table 1 for various time periods also indicated in Table 1. The plates in which the disinfecting liquid specimens Nos. 9-12 are accommodated, respectively, were left at room temperature for various time periods indicated in Table 1 without exposure to any light.

Thereafter, a soybean-casein-digest agar was poured into each of the plates in which the respective disinfecting liquid specimens were accommodated, and incubated at 32° C. Viable microorganism count per 1 mL of each of the disinfecting liquid specimens was calculated by counting colonies formed on the medium. Then, for each of the disinfecting liquid specimens, an amount of the reduction of the microbial challenge organism was calculated in logarithm (log reduction) according to the following equation. The results of calculation are indicated in Table 1:

Microbial challenge organism reduction amount [in logarithm]=log(viable microorganism count per 1 mL of each specimen immediately after inoculation)−log(viable microorganism count per 1 mL of each of the disinfecting liquid specimens).

TABLE 1

| | Disinfecting liquid specimens Nos. | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Metal phthalocyanine compound | | | | | | | | | | | | | |
| M | Cu | Fe | Fe | Zn | Al | Cu | Cu | — | Fe | Cu | — | Cu | Cu |
| Kind of substituents $R^1$-$R^8$ and number thereof | —H 4 —$NH_2$ 4 | —H 8 | —H 8 | —H 6 —$SO_3H$ 2 | —H 6 —$SO_3H$ 2 | —H 6 —$SO_3H$ 2 | —H 6 —$SO_3H$ 2 | — | —H 8 | —H 6 —$SO_3H$ 2 | — | —H 6 —$SO_3H$ 2 | —H 4 —$NH_2$ 4 |
| Concentration [ppm] | 80 | 50 | 50 | 20 | 20 | 1000 | 1000 | — | 50 | 1000 | — | 1000 | 80 |
| Concentration of $H_2O_2$ [ppm] | 20 | 30 | 30 | 20 | 20 | 300 | 300 | — | — | — | 300 | 300 | — |
| Concentration of $FeCl_3$ [ppm] | — | — | 30 | — | — | — | — | — | — | — | 50 | — | — |
| Light | | | | | | | | | | | | | |
| Light source | xenon lamp | xenon lamp | xenon lamp | xenon lamp | diode laser (HeNe) | fluorescent lamp | fluorescent lamp + red filter | xenon lamp | — | — | — | — | xenon lamp |
| Wavelength [nm] | 350-800 | 350-800 | 350-800 | 350-800 | 632.8 | 350-800 | 550-800 | 350-800 | — | — | — | — | 350-800 |

TABLE 1-continued

| | Disinfecting liquid specimens Nos. | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Intensity of light | 6000 [Lx] | 6000 [Lx] | 6000 [Lx] | 6000 [Lx] | 10 [mW/cm$^2$] | 4000 [Lx] | 3000 [Lx] | 6000 [Lx] | — | — | — | — | 6000 [Lx] |
| Irradiation time [hour] | 1 | 1 | 1 | 1 | 0.5 | 3 | 3 | 1 | 1* | 3* | 3* | 3* | 1 |
| microbial challenge organism reduction amount (log reduction) | 3.2 | 3.8 | 4.6 | 3.4 | 3.9 | >4.8 | >4.8 | 0.7 | 0.8 | 0.4 | 0.3 | 2.6 | 2.6 |

*The disinfecting liquid specimen was kept at room temperature for the time period without exposure to any light.

As is apparent from the results indicated in the above Table 1, in each of the disinfecting liquid specimens Nos. 1-7 which contained the metal phthalocyanine compound and the hydrogen peroxide according to the present invention and which had been irradiated with the corresponding lights, the log reduction value indicative of the amount of reduction of the bacteria was relatively large, so that the disinfecting liquid specimens according to the present invention exhibited a significantly high degree of disinfecting effect. Accordingly, it is recognized that a significantly high degree of disinfecting effect can be obtained by irradiating, with the light, the present disinfecting liquid in which the contact lens is immersed.

It is recognized from the comparison of the log reduction values of the disinfecting liquid specimens No. 2 and No. 3 that the disinfecting liquid specimen No. 3, including the Fe ion(s) that causes the Fenton reaction for promoting decomposition of the hydrogen peroxide, exhibited a significantly higher disinfecting effect than in the disinfecting liquid specimen No. 2 without containing the Fe ion(s).

In contrast, the disinfecting liquid specimens Nos. 8-13 exhibited lower disinfecting effects than the specimens Nos. 1-7 according to the present invention. This is because the specimens Nos. 8-13 were not prepared according to the present invention or not irradiated with the light.

As is apparent from the foregoing description, in the present method of disinfecting a contact lens, the contact lens is immersed in the contact lens disinfecting liquid which contains the metal phthalocyanine compound and the hydrogen peroxide, and the disinfecting liquid in which the contact lens is immersed is irradiated with the light. Accordingly, the present disinfecting method assures a synergistically enhanced disinfecting effect owing to the disinfecting effect exhibited by the metal phthalocyanine compound together with the disinfecting effect exhibited by the hydrogen peroxide.

What is claimed is:

1. A method of disinfecting a contact lens comprising the steps of:

preparing a disinfecting liquid comprising at least one metal phthalocyanine compound represented by the following formula (I) and hydrogen peroxide, wherein said at least one metal phthalocyanine compound is dissolved in an aqueous medium,

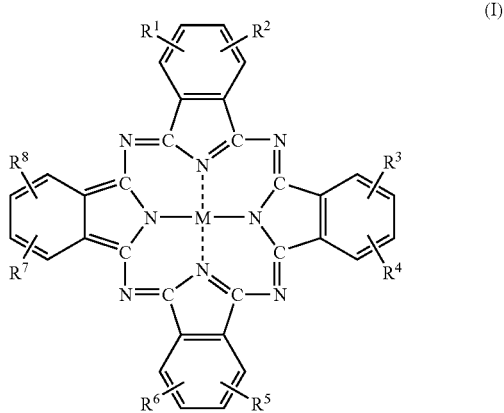

wherein M is zinc, aluminium, copper, iron, nickel, cobalt, gallium, aluminium chloride or gallium chloride, and each of $R^1$-$R^8$ is independently selected from a group consisting of a hydrogen atom, a halogen atom, a carboxyl group or an alkali metal or ammonium salt thereof, a sulfone group or an alkali metal or ammonium salt thereof, a quaternary ammonium group represented by the following formula (II), and an amine group represented by the following formula (III),

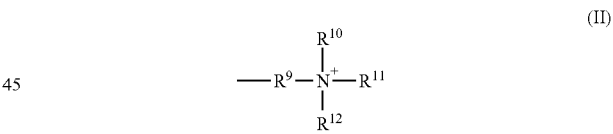

wherein $R^9$ is an alkylene group having 2-6 carbon atoms or an oxyalkylene group having 2-6 carbon atoms, and each of $R^{10}$-$R^{12}$ is independently selected from alkyl groups having 1-6 carbon atom(s),

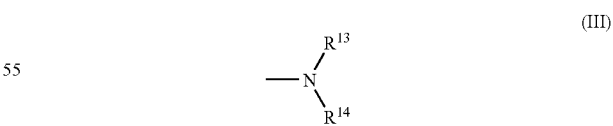

wherein each of $R^{13}$ and $R^{14}$ is independently selected from a group consisting of a hydrogen atom and —CO—A group in which A is an alkyl group having 7-17 carbon atoms, a vinyl group, 1-methylvinyl group, a methacryloyl group or an acryloyl group;

immersing a non-water absorptive contact lens in said disinfecting liquid; and irradiating said disinfecting liquid in which said non-water absorptive contact lens is immersed with a light.

2. A method according to claim 1, wherein said at least one metal phthalocyanine compound is present in said disinfecting liquid in a concentration in a range of 5-2000 ppm.

3. A method according to claim 1, wherein said hydrogen peroxide is present in said disinfecting liquid in a concentration in a range of 1-300 ppm.

4. A method according to claim 1, wherein said light with which said disinfecting liquid is irradiated has a wavelength in a range of 550-750 nm.

5. A method according to claim 1, wherein said disinfecting liquid further comprises at least one of a chelating agent, an isotonic agent, a buffer, a surfactant, a thickener, and a preservative.

6. A method according to claim 5, wherein said surfactant consists of at least one of an anionic surfactant and a nonionic surfactant.

7. A method according to claim 1, wherein said non-water absorptive contact lens is an oxygen-permeable contact lens.

8. A contact lens disinfecting liquid which exhibits a disinfecting effect with respect to a contact lens immersed therein when irradiated with a light, said contact lens disinfecting liquid consisting of an aqueous medium having an osmotic pressure in a range of 280-300 mOsm/Kg, an opthalmically physiologically compatible thickening agent, hydrogen peroxide in a concentration range of 1-300 ppm and at least one metal phthalocyanine compound dissolved therein, said at least one metal phthalocyanine compound being represented by the following formula (I),

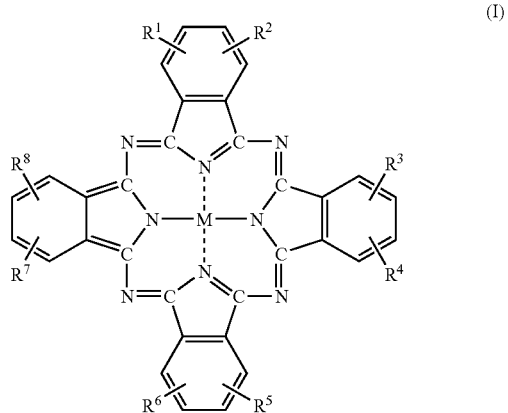

wherein M is zinc, aluminium, copper, iron, nickel, cobalt, gallium, aluminium chloride or gallium chloride, and each of $R^1$-$R^8$ is independently selected from a group consisting of a hydrogen atom, a halogen atom, a carboxyl group or an alkali metal or ammonium salt thereof, a sulfone group or an alkali metal or ammonium salt thereof, a quaternary ammonium group represented by the following formula (II), and an amine group represented by the following formula (III),

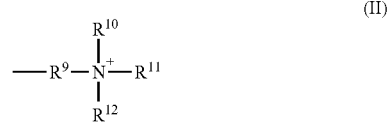

wherein $R^9$ is an alkylene group having 2-6 carbon atoms or an oxyalkylene group having 2-6 carbon atoms, and each of $R^{10}$-$R^{12}$ is independently selected from allyl groups having 1-6 carbon atom(s),

wherein each of $R^{13}$ and $R^{14}$ is independently selected from a group consisting of a hydrogen atom and —CO—A group in which A is an alkyl group having 7-17 carbon atoms, a vinyl group, 1-methylvinyl group, a methacryloyl group or an acryloyl group.

9. A contact lens disinfecting liquid according to claim 8, wherein said at least one phthalocyanine compound is present in said disinfecting liquid in a concentration in a range of 5-2000 ppm.

10. A contact lens disinfecting liquid according to claim 8, wherein said light with which said disinfecting liquid is irradiated has a wavelength in a range of 550-750 nm.

11. A contact lens disinfecting liquid according to claim 8, wherein said contact lens to be disinfected is an oxygen-permeable, non-water-absorptive contact lens.

12. A contact lens disinfecting liquid which exhibits a disinfecting effect with respect to a contact lens immersed therein when irradiated with a light, said contact lens disinfecting liquid consisting of an aqueous medium having an osmotic pressure in a range of 280-300 mOsm/Kg, hydrogen peroxide in a concentration range of 1-300 ppm and at least one metal phthalocyanine compound dissolved therein, said at least one metal phthalocyanine compound being represented by the following formula (I),

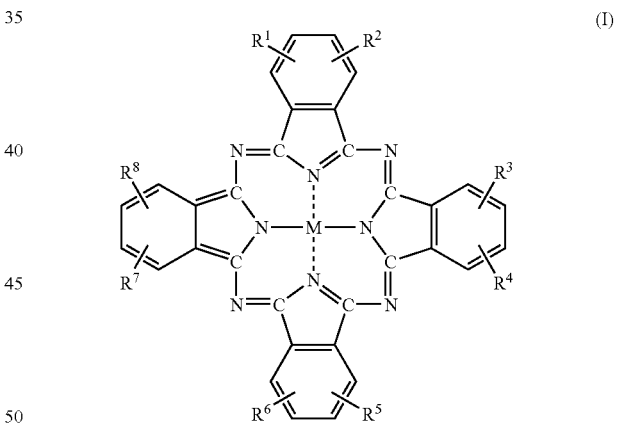

wherein M is zinc, aluminium, copper, iron, nickel, cobalt, gallium, aluminium chloride or gallium chloride, and each of $R^1$-$R^8$ is independently selected from a group consisting of a hydrogen atom, a halogen atom, a carboxyl group or an alkali metal or ammonium salt thereof, a sulfone group or an alkali metal or ammonium salt thereof, a quaternary ammonium group represented by the following formula (II), and an amine group represented by the following formula (III),

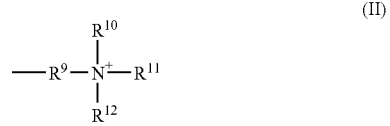

wherein $R^9$ is an alkylene group having 2-6 carbon atoms or an oxyalkylene group having 2-6 carbon atoms, and each of $R^{10}$-$R^{12}$ is independently selected from allyl groups having 1-6 carbon atom(s),

(III)

wherein each of $R^{13}$ and $R^{14}$ is independently selected from a group consisting of a hydrogen atom and —CO—A group in which A is an allyl group having 7-17 carbon atoms, a vinyl group, 1-methylvinyl group, a methacryloyl group or an acryloyl group.

13. The contact lens disinfecting liquid according to claim 8, wherein the thickening agent is provided in an amount of at least 0.01 w/v % to 10 w/v %.

* * * * *